United States Patent [19]

Matzik et al.

[11] Patent Number: 5,716,418
[45] Date of Patent: Feb. 10, 1998

[54] THE COLORING OF KERATIN-CONTAINING FIBERS WITH PREPARATIONS WHICH CONTAIN ALKYL GLYCOSIDES AND OXIDATION DYE PRECURSORS

[75] Inventors: Iduna Matzik, Erkrath; Horst Hoeffkes, Duesseldorf; Detlef Hollenberg, Erkrath; Reinhard Mueller, Erkelenz; Manuela Ehlert, Leverkusen; Christa Schramm, Duesseldorf, all of Germany

[73] Assignee: Henkel Kommanditgesellschaft auf Aktien, Duesseldorf, Germany

[21] Appl. No.: 617,532

[22] Filed: Mar. 15, 1996

Related U.S. Application Data

[63] Continuation of Ser. No. 387,885, Feb. 22, 1995, abandoned.

[30] Foreign Application Priority Data

Aug. 22, 1992 [DE] Germany .............. 42 27 864.3

[51] Int. Cl.⁶ .................................................. A61K 7/13
[52] U.S. Cl. .............................. 8/406; 8/435; 8/907
[58] Field of Search .......................... 8/404, 405, 406, 8/435, 561, 649, 913, 907

[56] References Cited

U.S. PATENT DOCUMENTS

| | | | |
|---|---|---|---|
| 4,517,174 | 5/1985 | Jacquet et al. | 8/405 |
| 4,919,846 | 4/1990 | Nakama et al. | 252/542 |
| 5,096,455 | 3/1992 | Grollier | 8/406 |
| 5,167,669 | 12/1992 | Grollier | 8/405 |
| 5,180,396 | 1/1993 | Grollier et al. | 8/406 |

FOREIGN PATENT DOCUMENTS

| | | |
|---|---|---|
| 0070074 | 1/1983 | European Pat. Off. |
| 0462857 | 12/1991 | European Pat. Off. |
| 0548620 | 6/1993 | European Pat. Off. |
| 4129926 | 7/1992 | Germany . |
| 61-5005 | 1/1986 | Japan . |
| 2186891 | 8/1987 | United Kingdom . |

OTHER PUBLICATIONS

English language translation of Yoshitomi, JP 61-5005, pp. 1-9, Jan. 1986.

*Primary Examiner*—Paul Lieberman
*Assistant Examiner*—Caroline L. Dusheck
*Attorney, Agent, or Firm*—Wayne C. Jaeschke; John E. Drach; Henry E. Millson, Jr.

[57] ABSTRACT

A composition and process for coloring keratin-containing fibers wherein the composition comprises: (a) an alkyl glycoside of the formula (I):

$$R^1\text{—}O\text{—}(G)_x\text{—}H \quad (I)$$

wherein $R^1$ is a linear or branched alkyl or alkenyl radical having from 12 to 16 carbon atoms, (G) is an anhydroglucose unit, and x is a number from about 1 to about 2.5; (b) an oxidation dye precursor; and (c) a water-based carrier.

16 Claims, No Drawings

THE COLORING OF KERATIN-CONTAINING FIBERS WITH PREPARATIONS WHICH CONTAIN ALKYL GLYCOSIDES AND OXIDATION DYE PRECURSORS

This application is a continuation of application Ser. No. 08/387,885 filed on Feb. 22, 1995, now abandoned.

BACKGROUND OF THE INVENTION

1. Field of the Invention

This invention relates to preparations for coloring keratin-containing fibers based on oxidation dyes containing a $C_{12-16}$ alkyl glycoside and, preferably, an amphoteric or zwitterionic polymer.

2. Statement of Related Art

Typical preparations for coloring keratin-containing fibers contain as their coloring component oxidation dye precursors which form the actual dye in the presence of oxidizing agents. In addition, they contain surfactants which are intended to guarantee the wetting of the fibers and adequate absorption of dye onto the fibers. The dyes typically used to impart good coloring properties to the coloring preparations are not always satisfactorily compatible with the skin. Accordingly, there has been no shortage of attempts to produce colorants containing skin-compatible surfactants which combine adequate foaming power with favorable coloring properties, for example in regard to dye absorption onto the fibers and levelling behavior.

Thus, EP-A-462 857 describes a hair colorant based on an oxidation dye containing a fatty alcohol ether sulfate and a $C_{8-10}$ alkyl glycoside.

EP 070 074 discloses foaming compositions containing alkyl polyglycoside and an anionic surfactant which may optionally contain dyes. However, there is no reference in this document to a colorant for keratin fibers.

DE 41 29 926 describes hair tinting shampoos based on substantive dyes containing a $C_{9-11}$ alkyl polyglycoside, an anionic surfactant and an amine oxide.

It has now been found that colorants based on oxidation dyes containing a $C_{12-16}$ alkyl glycoside combine excellent skin compatibility with very good coloring properties such as, for example, dye absorption onto the fibers and levelling. In addition, the hair colors thus obtained show very good fastness properties.

Description of the Preferred Embodiments

The present invention relates to preparations for coloring keratin-containing fibers containing an alkyl glycoside corresponding to formula (I):

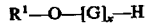

$$R^1-O-[G]_x-H \qquad (I)$$

in which $R^1$ is a linear or branched alkyl or alkenyl radical containing 12 to 16 carbon atoms, [G] is an anhydroglucose unit and x is a number of 1 to 2.5 and preferably 1.1 to 1.6, an oxidation dye precursor and a water-based carrier.

Keratin-fibers are, for example, human and animal hairs, pelts, wool or feathers.

Oxidation dye precursors are dye precursors which form the actual dyes under the influence of oxidizing agents or atmospheric oxygen in the course of an oxidative polymerization reaction. In addition to oxidation dye precursors of the primary intermediate type, those of the secondary intermediate type are advantageously used. Oxidation dye precursors of the secondary intermediate type couple with the precursors of the primary intermediate type during the polymerization reaction, thus enabling the required color tones to be obtained. Typical precursors of the primary intermediate type are primary aromatic amines containing another free or substituted hydroxy or amino group in the para position or ortho position, diaminopyridine derivatives, heterocyclic hydrazone derivatives, 4-aminopyrazolone derivatives, tetraaminopyrimidine derivatives and indole and indoline derivatives. Typical precursors of the secondary intermediate type are, for example, metaphenylene-diamine derivatives, dihydroxynaphthalenes, naphthols, resorcinol derivatives, meta-aminophenols and pyrazolones.

In the most simple case, the water-based carrier is water or a water/alcohol mixture, although it is preferably an emulsion, a gel or a surfactant-containing foaming solution.

The $C_{12-16}$ alkyl glycosides present in the coloring preparations according to the invention are distinctly superior to $C_{8-11}$ alkyl glycosides in regard to dye absorption onto the fibers. The color-intensifying effect and the resulting saving of dye during coloring unexpectedly reaches a maximum in the $C_{12-16}$ alkyl glycosides and thereafter begins to fall off again with the $C_{18}$-alkyl-substituted glycosides.

So far as the foaming behavior of the coloring preparations according to the invention is concerned, the $C_{12-16}$ alkyl glycosides may ideally be combined with other surfactants. Suitable other surfactants are anionic, cationic, nonionic, amphoteric and zwitterionic surfactants.

Anionic surfactants are, for example, fatty alkyl ether carboxylates, sulfosuccinates, oleic acid sulfonates, fatty alkyl ether citrates and tartrates, fatty acyl glutamates, fatty acyl isethionates, fatty acyl taurides, fatty acyl sarcosides, α-sulfofatty acids and salts thereof, sorbitan ester sulfates, hydroxyalkyl sorbitol citrates, soaps, fatty alkyl sulfates, alkane sulfonates and α-olefin sulfonates.

Cationic surfactants are, for example, $C_{12-18}$ alkyl trimethylammonium salts, $C_{12-18}$ alkyl dimethyl benzylammonium salts, cetyl pyridinium chloride, 2-hydroxydodecyl hydroxyethyl dimethylammonium chloride, $C_{12-18}$ dialkyl dimethylammonium salts and $C_{12-18}$ trialkyl methylammonium salts.

Nonionic surfactants are, for example, adducts of 5 to 30 moles of ethylene oxide with fatty alcohols, with alkylphenols, with fatty acids, with fatty acid alkanolamides, with fatty acid partial glycerides, with fatty acid sorbitan partial esters or with fatty acid methyl glucoside partial esters, also fatty acid polyglycerol esters and fatty acyl glucosamines.

Amphoteric surfactants are, for example, N-dodecyl aminoacetic acid, N-cetyl aminopropionic acid, gamma-lauryl aminobutyric acid.

Zwitterionic surfactants are, for example, $C_{12-18}$ alkyl dimethylammonium glycinate, cocoacyl aminopropyl dimethylammonium glycinate or imidazolinium betaines.

Because of possible impurities in the form of nitrosamines, amine oxides are preferably not used in the coloring preparations according to the invention.

So far as coloring properties are concerned, the alkyl glycosides corresponding to formula (I) are effective in only small quantities in the coloring preparations according to the invention. Accordingly, the present invention also relates to preparations for coloring keratin-containing fibers in which the alkyl glycoside corresponding to formula (I) is present in a quantity of 0.05 to 5% by weight and preferably in a quantity of 0.1 to 2.4% by weight, based on the coloring preparation as a whole.

Particularly good results, above all in regard to the wet combability of the dyed fibers and the fastness to washing of the colors obtained, are achieved when an amphoteric or zwitterionic polymer is added to the coloring preparation.

Accordingly, the present invention also relates to preparations for coloring keratin-containing fibers which additionally contain an amphoteric or zwitterionic polymer in a quantity of 0.02 to 5% by weight and preferably in a quantity of 0.1 to 2% by weight, based on the coloring preparation as a whole.

Suitable amphoteric polymers, but by no means the only amphoteric polymers usable in accordance with the invention, are for example amphoteric cellulose esters or copolymers of anionic and cationic vinyl monomers. Most particularly suitable polymers are the zwitterionic polymers obtained by quaternization of the reaction products of acrylamides, such as for example dimethylaminoethyl acrylamide, dimethylaminoethyl methacrylamide, dimethylaminopropyl acrylamide, dimethylaminopropyl methacrylamide, diethylaminoethyl acrylamide, dimethylaminoethyl acrylate, dimethylaminoethyl methacrylate or diethylaminoethyl acrylate, and acrylic acid or substituted acrylic acids, such as for example methacrylic acid, crotonic acid or 2-methyl crotonic acid.

It is not necessary to use a single polymer, instead mixtures of various amphoteric or zwitterionic polymers may also be used.

The coloring preparations according to the invention may optionally contain typical cationic polymers such as, for example, quaternized cellulose ethers, dimethyl diallylammonium homopolymers, dimethyl diallylammonium/acrylic acid and acrylamide copolymers, quaternized vinyl pyrrolidone/dimethylaminoethyl acrylate copolymers and copolymers of vinyl imidazolinium methochloride and vinyl pyrrolidone.

The coloring preparations according to the invention produce intensive hair colors at physiologically acceptable temperatures below 40° C. Accordingly, the coloring preparations are most particularly suitable for coloring human hair.

The present invention also relates to hair coloring preparations containing
- an alkyl glycoside corresponding to formula (I) in a quantity of 0.05 to 5% by weight and preferably in a quantity of 0.1 to 2.4% by weight,
- an oxidation dye precursor in a quantity of 0.01 to 5% by weight,
- an amphoteric or zwitterionic polymer in a quantity of 0.02 to 5% by weight and preferably in a quantity of 0.1 to 2% by weight, based on the hair coloring preparation as a whole, and
- a water-based carrier.

The water-based carrier is preferably a cream, an emulsion, a gel, a surfactant-containing foaming solution or any other preparation suitable for application to the hair.

Typical constituents of such carriers are formulation and coloring aids which increase the stability of the preparations and improve the result of coloring. Such additives are, for example, water-soluble thickening polymers (hydrocolloids), for example cellulose ethers, such as carboxymethyl cellulose, hydroxyethyl cellulose, methyl cellulose, methyl hydroxypropyl cellulose, starch and starch ethers, vegetable gums, guar gum, agar agar, alginates, xanthan gum or synthetic water-soluble polymers, oils and fatty materials in the broadest sense, for example paraffin oil, fatty acid esters, fatty alcohols and even, for example branched alcohols, such as 2-octyl-1-dodecanol or 2-hexyl-1-decanol, antioxidants, for example ascorbic acid, sodium sulfite, buffers, for example ammonium chloride or ammonium sulfates, complexing agents, for example 1-hydroxyethane-1,1-diphosphonic acid, nitrilotriacetic acid or ethylenediamine tetraacetic acid or salts thereof, hair-cosmetic auxiliaries, for example protein derivatives, glucose, D-panthenol, cholesterol, vitamins or plant extracts, levelling aids, for example urazole, hexahydropyrimidin-2-one, imidazole, 1,2,4-triazole or iodides, for example sodium or potassium iodide.

Irrespective of the nature of the cosmetic formulation, for example a cream, gel or shampoo, the hair coloring preparations according to the invention may be applied in a mildly acidic, neutral or alkaline medium. The hair coloring preparations are preferably applied at a pH value in the range from 6 to 10.

In addition to the compulsory oxidation dye precursors, typical substantive dyes may optionally be present in the hair coloring preparations for color toning purposes.

The hair coloring preparations according to the invention produce a fine creamy foam. They are toxicologically safe and highly compatible with the skin. Optimal compatibility with the skin is obtained when the claimed $C_{12-16}$ alkyl glycosides are used. They are superior both to the relatively short-chain $C_{8-11}$ alkyl glycosides and to the relatively long-chain $C_{18-22}$ alkyl glycosides.

Coloring properties, such as dye absorption capacity and levelling behavior, are excellent. The hair colors obtained are distinguished by their brilliance and their high fastness to washing. The colored hair is distinguished by very good wet combability.

The following Examples are intended to illustrate the invention without limiting it in any way.

EXAMPLES

A hair coloring cream base with the following composition (Table I) was prepared:

TABLE I

| | |
|---|---|
| Tallow fatty alcohol | 6.5 g |
| Cocofatty alcohol | 2.0 g |
| p-Tolylenediamine (primary intermediate) | 0.52 g |
| Resorcinol (secondary intermediate) | 0.10 g |
| 4-Chlororesorcinol (secondary intermediate) | 0.15 g |
| 3-Amino-2-methylamino-6-methoxypyridine (primary intermediate) | 0.03 g |
| Ammonium sulfate | 1.4 g |
| Sodium sulfite (inhibitor) | 0.5 g |
| Ascorbic acid (inhibitor) | 0.4 g |
| Paraffin oil | 0.2 g |
| Ammonia (30%) | 5.7 g |

The constituents were mixed together in the order shown. After addition of the additional components listed in following Examples 1 to 9, the primary intermediates and the inhibitors, a pH value of 9.5 was initially adjusted with the ammonia solution, followed by making up with water to 100 g.

(Table II)

Examples 1 to 9
(Examples 4 to 9 correspond to the invention)

| | 1 | 2 | 3 | 4 | 5 |
|---|---|---|---|---|---|
| $C_{12/16}$ fatty alcohol glycoside (Plantaren 1200)* | — | — | — | 2.4 g | 1.0 g |
| $C_{12/14}$ fatty alcohol 4.5 EO acetic acid, ammonium salt (Akypo RLM 45 A)** | — | 4.9 g | 3.5 g | 2.5 g | 2.9 g |
| Na lauryl ether sulfate (Texapon N 25)* | 4.9 g | — | 1.4 g | — | 1.0 g |

| | 6 | 7 | 8 | 9 |
|---|---|---|---|---|
| $C_{12/16}$ fatty alcohol glycoside (Plantaren 1200)* | 1.0 g | 1.0 g | 1.0 g | 2.4 g |
| $C_{12/14}$ fatty alcohol 4.5 EO acetic acid, ammonium salt (Akypo RLM 45 A)** | 2.9 g | 1.9 g | — | 2.5 g |
| Na lauryl ether sulfate (Texapon N 25)* | 1.0 g | 2.0 g | 3.9 g | — |
| Acrylic acid, Na salt/ acrylamidopropyl trimethyl-ammonium chloride copolymer (polymer P1 acc. to DE-OS 39 29 973) | 0.3 g | 0.3 g | 0.6 g | 0.6 g |

*A product of Henkel KGaA
**A product of Chem-Y

The oxidative development of the hair color was carried out with 6% hydrogen peroxide solution as oxidation solution. To this end, 50 g of hydrogen peroxide solution (6%) were added to and mixed with 50 g of the emulsion.

The coloring cream was applied to approximately 5 cm long strands of standardized, 90% grey, but not specially pretreatment human hair and left thereon for 30 minutes at 27° C. After the coloring process, the hair was rinsed, washed with a standard shampoo and then dried.

The color tone obtained with compositions 1 to 9 was light brown.

Levelling strands were colored in the same way; levelling strands were prepared as follows:

The upper half of the hair strand (hair tip) was treated for 30 minutes with an aqueous solution of a cold-wave preparation based on ammonium thioglycolate. After fixing (10 minutes, potassium bromate solution), the same half of the hair strand was bleached with an solution of hydrogen peroxide and ammonium peroxydisulfate. This was followed once more by treatment with the cold-wave preparation, fixing and bleaching. The lower half of the hair strand (root area) was bleached only once. Two strand halves "mistreated" to different extents were obtained in this way.

The results in regard to dye absorption, fastness to washing and levelling behavior of compositions 1 to 9 are set out in Table III.

Levelling behavior is expressed in the form of DE values (total color difference between the two ends of the levelling strands). The DE values were obtained as follows:

Each levelling hair strand was measured with a Datacolor color measuring system at eight places (4 in the vicinity of the hair root and 4 in the vicinity of the hair tip). To this end, the sample to be measured was fixed in a clamp to the spectral photometer and the reflectance values were measured over the visible light range from 390 to 700 nm at intervals of 10 nm and processed by computer (IBM-PS 2). The computer program determined the standard color values under the CIE system (Commission Internationale de l'Eclairage) in accordance with DIN 5033 and converted them into color difference values in accordance with DIN 6174.

Composition 1 was used as the standard in regard to dye absorption and fastness to washing. To this end, the color intensity of the unwashed strand dyed with composition 1 was colorimetrically determined and put at 100%. The relative color intensities of the unwashed hair strands colored with the other compositions 2 to 9 are shown in the "dye absorption" column of Table III.

The colorimetrically determined color intensity of the hair strands colored with composition 1 and washed six times was similarly put at 100%. The relative color intensities of the strands colored with compositions 2 to 9 are shown in the "fastness to washing" column of Table III.

(Note: Accordingly, comparisons of the relative color intensities are only permissible within one and the same column.)

TABLE III

| | Rel. color intensity of the of unwashed strand (Dye absorption) | Rel. color intensity the 6x washed strand (Fastness to washing) | DE Value of the 6x washed strand (Levelling) |
|---|---|---|---|
| 1 | 100% | 100% | 10.45 |
| 2 | 105% | 98% | 9.87 |
| 3 | 106% | 101% | 10.19 |
| 4 | 104% | 99% | 8.6 |
| 5 | 110% | 105% | 8.5 |
| 6 | 112% | 110% | 8.7 |
| 7 | 110% | 105% | 8.8 |
| 8 | 103% | 101% | 9.85 |
| 9 | 106% | 104% | 8.87 |

Coloring compositions 4 to 9 according to the invention show on average distinctly better results than comparison compositions 1 to 3 in regard to dye absorption, levelling and fastness to washing.

Wet combability, feel and shine are also distinctly improved in relation to the comparison compositions.

In another test, the cocofatty alcohol was replaced by 2-octyl-1-dodecanol in Examples 1 to 9. It was found that the cream preparations containing 2-octyl-1-dodecanol show increased stability at low temperatures.

The replacement of 1.0 g of cocofatty alcohol and the same quantity of tallow fatty alcohol by 2.0 g of 2-octyl-1-dodecanol in Examples 1 to 9 produced the same result.

What is claimed is:

1. A hair coloring preparation comprising: (a) from about 0.05 to about 5% by weight of an alkyl glycoside of the formula (I):

$$R^1\text{—O—}(G)_x\text{—H } [R^1\text{—O—}[G]_x\text{—H}] \tag{I}$$

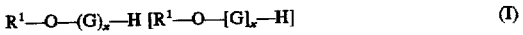

wherein $R^1$ is a linear or branched alkyl or alkenyl radical having from 12 to 16 carbon atoms, (G) is an anhydroglucose unit, and x is a number from about 1 to about 2.5; (b) from about 0.01% to about 5.0% by weight of an oxidation dye precursor; and (c) a water-based carrier.

2. The preparation of claim 1 wherein x is from about 1.1 to about 1.6.

3. The preparation of claim 1 wherein the amount of said alkyl glycoside in said preparation is from about 0.1 to about 2.4% by weight.

4. The preparation of claim 1 further comprising an amphoteric or zwitterionic polymer or a mixture thereof.

5. The preparation of claim 4 wherein the amount of said polymer in said preparation is from about 0.02 to about 5% by weight.

6. The preparation of claim 5 wherein the amount of said polymer in said preparation is from about 0.1 to about 2% by weight.

7. The preparation of claim 1 wherein component (c) is either water, a water/alcohol mixture, an emulsion, a cream, a gel, or a surfactant-containing foaming solution.

8. The preparation of claim 1 further comprising at least one additional surfactant selected from the group consisting of anionic, cationic, nonionic, amphoteric, and zwitterionic surfactants.

9. The preparation of claim 1 further comprising a cationic polymer.

10. The preparation of claim 1 further comprising from about 0.02% to about 5% by weight of an amphoteric surfactant, a zwitterionic surfactant, or a mixture thereof.

11. The preparation of claim 10 wherein from about 0.1 to about 2% by weight of the amphoteric surfactant, zwitterionic surfactant or mixture of such surfactants is present therein.

12. The preparation of claim 1 further comprising at least one of a water-soluble thickening polymer, an oil or fatty material, an antioxidant, a buffer, a complexing agent, a levelling aid, and a hair-cosmetic auxiliary.

13. The preparation of claim 1 wherein in the alkyl glycoside of formula I, x is from about 1.1 to about 1.6; the amount of alkyl glycoside is from about 0.1 to about 2.4% by weight; and the preparation further comprises from about 0.02 to about 5% by weight of an amphoteric surfactant, a zwitterionic surfactant, or a mixture thereof.

14. A process for coloring hair comprising treating hair with a coloring-effective quantity of the preparation of claim 1.

15. A process for coloring hair comprising treating hair with a coloring effective quantity of the preparation of claim 13.

16. The process of claim 14 wherein the process is carried out at a temperature of less than 40° C. and the preparation has a pH in the range of from about 6 to about 10.

\* \* \* \* \*